United States Patent

Banks et al.

[11] Patent Number: 4,992,424
[45] Date of Patent: Feb. 12, 1991

[54] ANTIPARASITIC AVERMECTIN DERIVATIVES

[75] Inventors: Bernard J. Banks; Michael J. Witty, both of New York, N.Y.

[73] Assignee: Pfizer Inc., New York, N.Y.

[21] Appl. No.: 320,209

[22] Filed: Mar. 7, 1989

[30] Foreign Application Priority Data

Mar. 26, 1988 [GB] United Kingdom ................ 8807280

[51] Int. Cl.$^5$ ...................... A61K 31/70; C07H 17/04
[52] U.S. Cl. ......................................... 514/30; 536/7.1
[58] Field of Search ........................... 514/30; 536/7.1

[56] References Cited

FOREIGN PATENT DOCUMENTS 0214731 3/1987 European Pat. Off. .
0284176 9/1988 European Pat. Off. .

Primary Examiner—Johnnie R. Brown
Assistant Examiner—Elli Peselev
Attorney, Agent, or Firm—Peter C. Richardson; J. Trevor Lumb; Gregg C. Benson

[57] ABSTRACT

Broad spectrum antiparasitic agents of formula (I) having utility as anthelmintics, ectoparasiticides, insecticides, acaricides and animal growth promotants

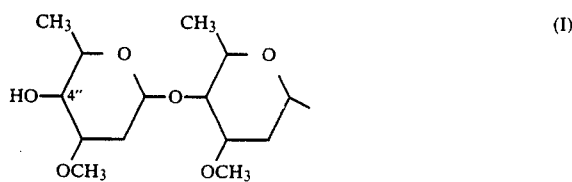

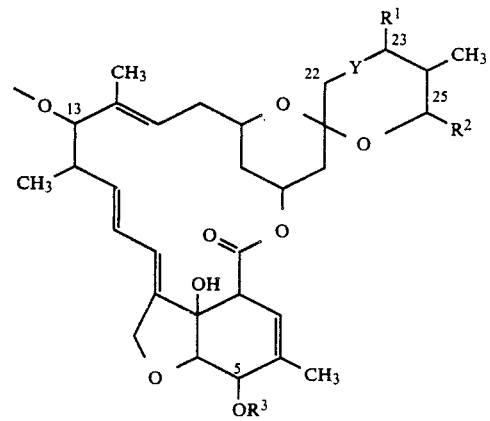

wherein Y is a single bond or a double bond; $R^1$ is OH; provided that when Y is a single bond $R^1$ is present and when Y is a double bond $R^1$ is absent; $R^2$ is $=CH_2$ or a group of the formula $-(X)-C(R^5)=CHR^6$; $R^3$ is H or $CH_3$; $R^5$ and $R^6$ are both H; $R^5$ is H and $R^6$ is $C_1-C_3$ alkyl; or one of $R^5$ and $R^6$ is H and the other is $C_2-C_6$ alkoxycarbonyl, phenyl, substituted phenyl, heteroaryl or substituted heteroaryl; and X is a direct bond or an alkylene group having from 2 to 6 carbon atoms which may be straight or branched-chain; with the proviso that $R^5$ and $R^6$ are not both hydrogen when X is $-CH(CH_3)CH_2-$; processes and intermediates therefor, and compositions thereof.

20 Claims, No Drawings

ANTIPARASITIC AVERMECTIN DERIVATIVES

BACKGROUND OF THE INVENTION

1. Field of the Invention

This invention relates to antiparasitic agents and in particular to compounds related to the avermectins but having a novel substituent group at the 25-position and to processes for their preparation and compositions thereof.

2. Description of Related Art

The avermectins are a group of broad spectrum antiparasitic agents referred to previously as the C-076 compounds. They are produced by fermenting a strain of the microorganism *Streptomyces avermitilis* under aerobic conditions in an aqueous nutrient medium containing inorganic salts and assimilable sources of carbon and nitrogen. The isolation and the chemical structure of the eight individual components which make up the C-076 complex is described in detail in British Patent Specification No. 1573955.

In our European Patent Applications publication Nos. 0214731 and 0284176 and in British Patent Application No. 8726730, the counterpart of U.S. application Ser. No. 249,749, filed Sept. 27, 1988, we describe the preparation of compounds related to the avermectins but having an unnatural substituent group at the 25-position in place of the isopropyl or sec-butyl group which is present in the naturally occurring avermectins.

SUMMARY OF THE INVENTION

The present invention provides a further series of semi-synthetically derived novel compounds wherein the 25-position substituent is an alkenyl or substituted alkenyl group. The compounds possess a broad spectrum of activity against insect pests, acari, free-living nematodes and parasites affecting humans and animals.

Thus, according to the present invention there are provided compounds having the formula:

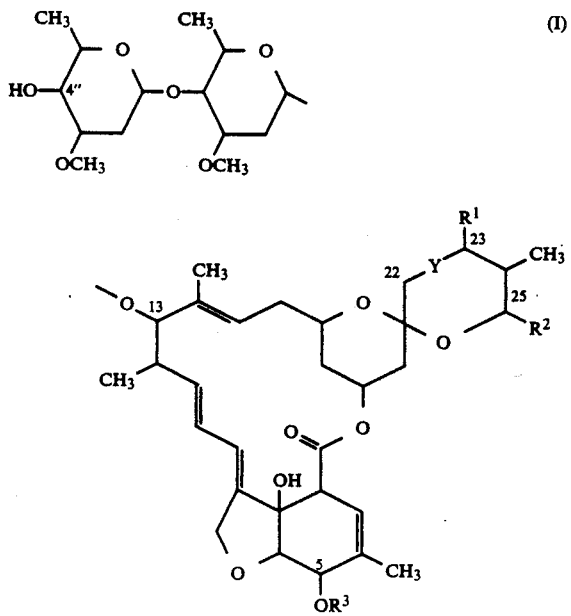

wherein Y is a single bond or a double bond; $R^1$ is OH; provided that when Y is a single bond $R^1$ is present and when Y is a double bond $R^1$ is absent; $R^2$ is $=CH_2$ or $—(X)—C(R^5)=CHR^6$; $R^3$ is H or $CH_3$; $R^5$ and $R^6$ are both H; $R^5$ is H and $R^6$ is $C_1$-$C_3$ alkyl; or one of $R^5$ and $R^6$ is H and the other is $C_2$-$C_6$ alkoxycarbonyl, phenyl, substituted phenyl, heteroaryl or substituted heteroaryl wherein said substituent is fluorine, chlorine, $C_1$-$C_4$ alkyl, $C_1$-$C_4$ alkoxy, $C_1$-$C_4$ alkylthio, hydroxy($C_1$-$C_4$)alkyl, cyano, aminosulphonyl, $C_2$-$C_6$ alkanoyl, $C_2$-$C_6$ alkoxycarbonyl, nitro, trifluoromethyl, trifluoromethoxy, amino or mono or di-$C_1$-$C_4$ alkylamino; and X is a direct bond or an alkylene group having from 2 to 6 carbon atoms which may be straight or branched-chain; with the proviso that $R^5$ and $R^6$ are not both hydrogen when X is $—CH(CH_3)CH_2—$.

The invention also includes compounds of the formula (I) above wherein $R^1$ and $R^3$ are as previously defined and $R^2$ is a group of the formula:

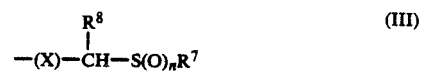

wherein X is as previously defined; $R^7$ is $C_1$-$C_4$ alkyl; $R^8$ is H or $C_1$-$C_4$ alkyl; and n is 1 or 2. These compounds are synthetic intermediates for the compounds of formula (I) wherein $R^2$ is $=CH_2$ or $—(X)—CR^5=CHR^6$ as well as being active antiparasitic agents in their own right.

In the above definitions, alkyl groups containing 3 or more carbon atoms may be straight or branched chain.

The term heteroaryl means a 5 or 6 membered aromatic heterocyclic group containing as heteroatom one or more atoms selected from nitrogen, oxygen and sulphur. The heteroaryl group may be unsubstituted, benzofused or substituted as previously defined. Particular examples include pyridyl, thienyl, furanyl, indolyl, pyrimidinyl and benzothienyl.

Preferred compounds include those derivatives wherein $R^2$ is $—CH=CH_2$ or $—CH=CH—R^6$ wherein $R^6$ is substituted phenyl, particularly where $R^6$ is 4-trifluoromethoxyphenyl; the avermectin B1 derivatives wherein $R^3$ is hydrogen, $R^1$ is absent and the 22,23 double bond is present being especially preferred.

The C-076 complex comprises eight distinct but closely related compounds described as C-076 A1a, A1b, A2a, A2b, B1a, B1b, B2a and B2b. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively, and the numeral "1" refers to avermectins wherein a double bond is present at the 22-23 position, and numeral "2" to avermectins lacking the 22-23 double bond and having a hydrogen at the 22-position and hydroxy at the 23 position.

In this specification, the "a" and "b" identifiers have been dropped, however, identifiers A1, A2, B1 and B2 have been retained to refer to non-natural avermectins having the structural features corresponding to those of the natural avermectins as noted above.

DETAILED DESCRIPTION OF THE INVENTION

The compounds of formula (I) are prepared by a number of different processes according to the invention:

(a) Compounds of the formula (I) wherein $R^2$ is $=CH_2$ or $—(X)—CH=CHR^6$, wherein $R^6$ is H or $C_1$-$C_3$ alkyl, are prepared from the corresponding C-25 alkylthioalkyl compound of formula (I) wherein $R^2$ is:

  (II)

wherein X is as previously defined; $R^7$ is $C_1$-$C_4$ alkyl and $R^8$ is H or $C_1$-$C_4$ alkyl; by a process which involves, first oxidation to give the corresponding sulphoxide or sulphone wherein $R^2$ is:

  (III)

wherein n is 1 or 2, followed in the case of the sulphoxides by a thermal elimination or, in the case of the sulphones, by a base catalysed elimination reaction.

The oxidation step is achieved in a conventional manner by treating the alkyl-sulphide, in solution, with an oxidising agent. A variety of oxidants may be used for this step but for best results for preparation of the sulphoxides, a reagent is used which avoids over-oxidation to the sulphone. Thus, preferred oxidants would be for example meta-chloroperbenzoic acid, tertiary-butyl hypochlorite or sodium metaperiodate, meta-chloroperbenzoic acid being the reagent of choice. The reaction is generally achieved by adding one equivalent of the oxidant to a cooled solution of the sulphide in an inert organic solvent, for example dichloromethane. The course of the reaction can be followed by thin layer chromatography and the reaction is generally substantially complete after several hours. Excess oxidant is destroyed, for example by the addition of dimethylsulphide, and the product is then isolated in a conventional manner and further purified, if desired, by chromatography. The sulphones can be prepared following a similar procedure but using excess oxidising agent for a longer period of time.

The elimination step to give the alkene is generally achieved by heating the sulphoxide in a high-boiling organic solvent, for example by heating in 1,2,4-trichlorobenzene at 175° C. for a period of one or two hours. Again the product is isolated in a conventional manner, typically by adsorption onto a silica column, followed by elution with an appropriate solvent. Further purification can be achieved, if desired, by column chromatography or high pressure liquid chromatography.

In the case where the elimination reaction is performed using a compound wherein $R^2$ is a sulphoxide of formula (III) wherein X is a direct bond and $R^8$ is hydrogen, the resulting product is the corresponding compound of formula (I) wherein $R^2$ is $=CH_2$ (an exocyclic methylene group). A preferred sulphoxide for use in this process is the 1-methylsulphinylmethyl derivative.

Another preferred $R^2$ group for use in the elimination reaction is the 1-methylsulphinylethyl which yields compounds of formula (I) wherein $R^2$ is ethenyl.

The intermediate sulphoxides and sulphones of formula (I) wherein $R^2$ is as defined in formula (III), in addition to being useful synthetic intermediates are also active anti-parasitic agents in their own right and form a further aspect of this invention.

The starting C-25 alkylthioalkyl avermectin derivatives of formula (I) wherein $R^2$ is as defined by formula (II) are prepared by adding the appropriate alkylthioalkyl carboxylic acid to a fermentation of an avermectin producing organism as described in EP-A-0214731, EP-A-0284176 or British patent application No. 8726730.

EP-A-0214731 and EP-A-0284176 describe fermentation of avermectin producing Streptomyces avermitilis organisms and certain mutants thereof in the presence of a carboxylic of the general formula $RCO_2H$ or a salt, ester or amide thereof, or an oxidative precursor therefor, wherein R is, inter alia, an alpha-branched $C_3$-$C_8$ alkylthioalkyl group, to produce certain corresponding C-25 alkythioalkyl avermectin compounds. British patent application No. 8726730 describes the fermentation of Streptomyces avermitilis ATCC 53567 and ATCC 53568 in the presence of a carboxylic acid of the general formula $RCH_2CO_2H$ or a salt, ester or amide thereof, or an oxidative precursor therefor, wherein R is, inter alia, alkylthioalkyl where each alkyl group contains 1 to 6 carbon atoms, to produce certain corresponding C-25 alkylthio alkyl avermectin compounds.

(b) Compounds of the formula (I) wherein $R^2$ is of formula —(X)—$CR^5$=$CHR^6$ and $R^5$ is H and $R^6$ is $CH_3$, may be obtained by an isomerisation reaction from the corresponding compound of formula (I) wherein $R^2$ is an alkenyl group containing a terminal double bond. The isomerisation can be achieved with, for example, a rhodium or iridium containing organometallic catalyst in accordance with established literature procedures.

Thus, for example, compounds of the formula (I) wherein $R^2$ is 1-methyl-trans-but-2-enyl (X=—CH($CH_3$)—, $R^5$=H, $R^6$=$CH_3$) can be obtained from the corresponding compounds wherein $R^2$ is 1-methyl-but-3-enyl. The isomerisation is readily achieved by contacting the starting terminal olefin, in solution with, for example, 1,5-cyclooctadienebis(methyldiphenylphosphine)iridium hexafluorophosphate, under an atmosphere of hydrogen for ten or fifteen minutes followed by several hours at room temperature under an inert atmosphere. The product is isolated by removal of the catalyst and evaporation of the solvent and further purification can be achieved, if necessary, by conventional procedures.

The starting compounds of formula (I) wherein $R^2$ is an alkenyl group containing a terminal double bond may be obtained by adding an appropriate unsaturated carboxylic acid to a fermentation of an avermectin producting organism as described in EP-A-0214731, EP-A-0284176 or British patent application No. 8726730. Thus, for example, feeding 2-methyl-pent-4-enoic acid provides the compounds of formula (I) wherein $R^2$ is 1-methyl-but-3-enyl.

(c) Compounds of the formula (I) wherein $R^2$ is —(X-)—$CR^5$=$CHR^6$, and one of $R^5$ and $R^6$ is H and the other is $C_2$-$C_6$ alkoxycarbonyl or substituted or unsubstituted phenyl or heteroaryl, are prepared from the corresponding compounds of formula (I) where $R^2$ is:

  (IV)

by a palladium catalysed reaction with a compound of the formula $R^9$-L wherein $R^9$ is $C_2$-$C_6$ alkoxy carbonyl or substituted or unsubstituted phenyl or heteroaryl and L is a suitable leaving group, e.g. bromine, iodine or organomercury. Appropriate reagents and conditions for this reaction (the Heck reaction), are described for example in Organic Reactions published by John Wiley & Sons, Volume 27 (1982). Typically the compound of formula (I) wherein $R^2$ is as defined by formula (IV)

above, in an organic solvent, e.g. acetonitrile, is warmed with an excess of an aryl or heteroaryl halide, generally the iodide, or an acyl halide, generally the chloride, in the presence of palladium acetate and a tertiary amine. The reaction is generally complete after 24 hours at a temperature of 50°-60° C. and the product is then isolated and purified by conventional techniques. In the case of the alkoxycarbonyl compounds, the reaction is best performed using an alkoxycarbonyl mercuric compound, e.g. the acetate at room temperature.

When the linking group X is a direct bond, the major component is of formula (I) wherein $R^5$ is hydrogen and $R^6$ is as defined for $R^9$. When the group X is present, for example as —$CH(CH_3)CH_2$—, the reaction product contains more equal amounts of the two possible isomers.

The starting materials of formula (I) wherein $R^2$ is as defined by formula (IV) above are obtained either directly from fermentation as previously described or from the corresponding C-25 alkylthioalkyl compound as described in process (a) above.

As previously mentioned the compounds of the invention are highly active antiparasitic agents having particular utility as anthelmintics, ectoparasiticides, insecticides, acaricides and animal growth promotants.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars, fire ants, termites and against migratory orthopterans such as locusts.

The compounds of formula (I) are administered as a formulation appropriate to the specific use envisaged and to the particular species of host animal being treated and the parasite or insect involved. For use as an anthelmintic the compounds are preferably administered by injection, either subcutaneously or intramuscularly, alternatively they may be administered orally in the form of a capsule, bolus, tablet or liquid drench, or they may be administered as a pour-on formulation or as an implant. Such formulations are prepared in a conventional manner in accordance with standard veterinary practice. Thus injectable formulations may be prepared in the form of a sterile solution or emulsion. Capsules, boluses or tablets may be prepared by mixing the active ingredient with a suitable finely divided diluent or carrier, additionally containing a disintigrating agent and/or binder such as starch, lactose, talc, or magnesium stearate. A drench formulation may be prepared by dispersing the active ingredient in an aqueous solution together with dispersing or wetting agents. These formulations will vary with regard to the weight of active compound depending on the species of host animal to be treated, the severity and type of infection and the body weight of the host. Generally for oral or parenteral administration, a dose of from about 0.001 to 10 mg per kg, preferably 0.01 to 1 mg/kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests, the compounds are applied as sprays, dusts, emulsions pour-on formulations and the like in accordance with standard agricultural practice.

For use as a growth promotant or for improving the lean meat to fat ratio in farm or domestic animals, the compounds may be administered with the animal feedstuff or drinking water. Alternatively they may be administered orally in the form of a capsule, bolus, tablet or liquid drench, or parenterally by injection or as an implant. Such formulations are prepared in a conventional manner in accordance with standard veterinary practice.

For human use the compounds are administered as a pharmaceutically acceptable formulation in accordance with normal medical practice.

The invention is illustrated by the following Examples in which Examples 1–4 describe the preparation of compounds of formula (I) wherein $R^2$ is as defined in formula (III) and Examples 5–29 describe preparation of compounds of formula (I).

Fast atom bombardment (FAB) mass spectrometry was performed on a VG Model 7070E mass spectrometer using a sample matrix of glycerol, thioglycerol, water and sodium chloride. Electron impact (EI) mass spectrometry was performed using a VG model 7070E mass spectrometer. m/z values are quoted for the principal fragments. $^1H$ Nuclear magnetic resonance (NMR) spectral data were obtained on a Nicolet QE 300 spectrometer with a sample concentration of 5 mg/ml in deuteriochloroform. The chemical shifts are given in parts per million relative to tetramethylsilane.

EXAMPLE 1

25-(1-Methylsulphinylethyl)-avermectin B1 (formula I; $R^1$=H, 22,23-double bond present, $R^2$=—$CH(CH_3)SOCH_3$, $R^3$=H)

A solution of meta-chloroperbenzoic acid (0.44 g, 85%) in dichloromethane (7 ml) was added dropwise to a stirred, cooled solution of 25-(1-methylthioethyl)-avermectin B1 (1.64 g) in dichloromethane (40 ml) at −70° C. After 5 hours, t.l.c. showed no starting material remaining. Several drops of dimethylsulphide were added and the mixture was allowed to warm to room temperature. The solution was then extracted with saturated aqueous sodium bicarbonate solution, and the organic phase dried over sodium sulphate and evaporated to yield the product as an oil (1.57 g, 95%) which was generally used for the next stage without further purification. Purification, when required, was carried out by adsorbing the product, in dichloromethane, onto a Waters silica Sep-Pak (trade mark) column, washing with ethyl acetate and then eluting the product with chloroform containing 5% methanol. The solution was evaporated and the residue was re-dissolved in aqueous methanol. Evaporation gave the required product as a white solid containing a mixture of epimeric diastereomers which could be further resolved by reverse-phase high-pressure liquid chromatography if required.

FAB mass spectrometry: (M+Na+) observed at m/z 929 (theoretical 929).

EI mass spectrometry: 261, 256, 242, 236, 227, 145, 113 and 87.

$^1$H NMR as expected for a B1 avermectin with characteristic peaks for the C-25 side-chain at 2.62 (3H, s, SOCH$_3$), 1.55 (3H, d, CH(C$\underline{H}_3$)SOCH$_3$).

EXAMPLE 2

25-(1-Methylsulphinylethyl)-avermectin A2 (formula I; $R^1$=OH, double bond absent, $R^2$=—CH(CH$_3$)SOCH$_3$, $R^3$=CH$_3$)

This was prepared as described in Example 1, using meta-chloroperbenzoic acid (0.055 g, 85%) and 25-(1-methylthioethyl)-avermectin A2 (0.176 g) to yield 184 mg of the title product as a white powder after evaporation from aqueous methanol. The product is a mixture of epimeric diastereomers which can be further resolved by reverse-phase liquid chromatography if required.

FAB mass spectrometry: (M+Na+) observed at m/z 961 (theoretical 961).

EI mass spectrometry: 588, 536, 511, 339, 275, 145, 113 and 87.

$^1$H NMR as expected for an A2 avermectin with characteristic peaks for the C-25 side-chain at 2.65 (3H, s, SOCH$_3$), 1.55 (3H, d, CH(C$\underline{H}_3$)SOCH$_3$).

EXAMPLE 3

25-Methylsulphinylmethyl-avermectin A2 (formula I, $R^1$=OH, double bond absent, $R^2$=—CH$_2$SOCH$_3$, $R^3$=CH$_3$)

This compound was prepared as described in Example 1 starting from 25-methylthiomethyl-avermectin A2 (0.050 g). The product (0.048 g) was obtained as a mixture of epimeric diastereomers which could be further resolved by reverse-phase liquid chromatography.

FAB mass spectrometry: (M+Na+) observed at m/z 947 (theoretical 947).

EI mass spectrometry: 307, 275, 244, 225, 145, 113, 87.

$^1$H NMR as expected for an A2 avermectin with characteristic peaks for the C-25 side-chain at 2.62 and 2.76 (3H, 2s, SOCH$_3$).

EXAMPLE 4

25-(1-Methylsulphonylethyl)-avermectin A2 (formula I; $R^1$=OH, double bond absent, $R^2$=—CH(CH$_3$)SO$_2$CH$_3$, $R^3$=CH$_3$)

A solution of meta-chloroperbenzoic acid (0.006 g, 85%) in dichloromethane (0.3 ml) was added dropwise to a stirred, cooled solution of 25-(1-methylthioethyl)-avermectin A2 (0.015 g) in dichloromethane (4 ml) at −70° C. The reaction mixture was allowed to warm to −18° C. and stirred at that temperature overnight. Several drops of dimethylsulphide were added and the mixture was allowed to warm to room temperature. The solution was then extracted with saturated aqueous sodium bicarbonate solution, and the organic phase dried over sodium sulphate and evaporated to yield the product as an oil (13 mg). The crude product was purified by reverse-phase high-pressure liquid chromatography on a Beckman Ultrasphere ODS (trade mark) C18 column eluting with 30% aqueous methanol. Evaporation of the appropirate fractions gave the product as a white solid (9 mg).

FAB mass spectrometry: (M+Na+) observed at m/z 977 (theoretical 977).

EI mass spectrometry: 648, 373, 355, 337, 289, 261, 243, 145, 113, 87.

$^1$H NMR as expected for a A2 avermectin with characteristic peaks for the C-25 side-chain at 3.0 (3H, s, SO$_2$C$\underline{H}_3$), 1.55 (3H, d, CH(C$\underline{H}_3$)SO$_2$CH$_3$).

EXAMPLE 5

25-Ethenyl-avermectin B1 (formula I; $R^1$=H, 22,23-double bond present, $R^2$=CH$_2$=CH—, $R^3$=H)

A stirred solution of 25-(1-methylsulphinylethyl)-avermectin B1 (0.077 g) in 1,2,4-trichlorobenzene (3 ml) containing reprecipitated calcium carbonate (140 mg) was heated at 175° C. under nitrogen for 1 hour. The mixture was cooled, diluted with dichloromethane and filtered. The filtrate was passed through a short silica column. The column was washed with dichloromethane and then the product was eluted using ethyl acetate. Evaporation of the ethyl acetate gave the required product as an oil (66 mg). The crude product (90% pure) was purified by reverse-phase high-pressure liquid chromatography on a Dupont Zorbax (trade mark) ODS C18 column eluting with a 23:77 mixture of water:methanol. Evaporation of the appropriate product containing fractions of the eluant gave the product as a white powder.

FAB mass spectrometry: (M+Na+) observed at m/z 865 (theoretical 865).

EI mass spectrometry: 536, 275, 191, 163, 145, 139, 113, 95 and 87.

$^1$H NMR as expected for a B1 avermectin with characteristic peaks for the C-25 side-chain at 5.85 (1H, m, C$\underline{H}$=CH$_2$), 5.3 (2H, m, CH=C$\underline{H}_2$).

EXAMPLE 6

25-Ethenyl-avermectin A2 (formula I, $R^1$=OH, double bond absent, $R^2$=—CH=CH$_2$, $R^3$=CH$_3$)

This was prepared as described in Example 5 but starting with 25-(1-methylsulphinylethyl)-avermectin A2 (0.68 g) and heating in 1,2,4-trichlorobenzene (27 ml) containing reprecipitated calcium carbonate to yield the required product as an oil (490 mg after work-up). The crude product (90% pure) was purified by reverse-phase liquid chromatography on a Dynamax (trade mark) 60-A C18 column eluting with a 23:77 mixture of water:methanol. Evaporation of the appropriate product containing fractions of the eluant gave the product as a white powder.

FAB mass spectrometry: (M+Na+) observed at m/z 897 (theoretical 897).

EI mass spectrometry: 568, 293, 275, 209, 179, 163, 145, 127, 113, 95 and 87.

$^1$H NMR as expected for a A2 avermectin with characteristic peaks for the C-25 side-chain at 5.8 (1H, m, C$\underline{H}$=CH$_2$), 5.3 (2H, m, CH=C$\underline{H}_2$).

EXAMPLE 7

25-Exo-methylenyl-avermectin A2 (formula I, $R^1$=OH, double bond absent, $R^2$==$CH_2$, $R^3$=$CH_3$)

A stirred solution of 25-methylsulphinylmethyl-avermectin A2 (0.020 g) in 1,2,4-trichlorobenzene (5 ml) containing reprecipitated calcium carbonate (20 mg) was heated at 175° C. under nitrogen for 2 hours. The mixture was cooled, diluted with dichloromethane and filtered. The filtrate was passed through a short silica column. The column was washed with dichloromethane and then the product was eluted using ethyl acetate. Evaporation of the ethyl acetate gave the required product as an oil (17 mg). The crude product (55% pure) was purified by reverse-phase chromatography on a Beckman Ultrasphere (trade mark) ODS C18 column eluting with a 28:72 mixture of water:methanol. Evaporation of the appropriate product containing fractions of the eluant gave the product as a white powder (5 mg).

FAB mass spectrometry: (M+Na+) observed at m/z 883 (theoretical 883).

EI mass spectrometry: 441, 405, 325, 315, 261, 171, 159, 145, 113, 95 and 87.

$^1$H NMR as expected for a A2 avermectin with characteristic peaks for the C-25 side-chain at 4.76 (1H, s, =CH($\underline{H}$)), 4.52 (1H, s, =C$\underline{H}$(H)).

EXAMPLE 8

25-(1-Methyl-trans-but-2-enyl)-avermectin A2 (formula I, $R^1$=OH, double bond absent, $R^2$=trans-CH($CH_3$)—CH=CH—$CH_3$, $R^3$=$CH_3$)

A solution of 25-(1-methylbut-3-enyl)-avermectin A2 (100 mg) in dry tetrahydrofuran (15 ml) containing a suspension of 1,5-cyclooctadienebis(methyldiphenylphosphine)iridium hexafluorophosphate (1 mg) was stirred at room temperature under an atmosphere of hydrogen for 10 minutes. The hydrogen was replaced with nitrogen and the solution was stirred for a further two hours and the solvent then evaporated. The crude product was purified by reverse-phase liquid chromatography on a Dupont Zorbax (trade mark) ODS C18 column eluting with a 25:75 mixture of water:methanol. Evaporation of the appropriate product containing fractions of the eluant gave the product as a white powder (60 mg).

FAB mass spectrometry: (M+Na+) observed at m/z 939 (theoretical 939).

EI mass spectrometry: 610, 335, 317, 275, 257, 251, 233, 223, 205, 181, 179, 145, 139, 113, 95 and 87.

$^1$H NMR as expected for an A2 avermectin with characteristic peaks for the C-25 side-chain at 5.47–5.59 (1H, dq, =C$\underline{H}$—$CH_3$), 1.78 (3H, d, =CH—$CH_3$).

EXAMPLES 9–22

25-(2-Phenylethenyl)-avermectin A2 (formula I, $R^1$=OH, double bond absent, $R^2$=—CH=CH$C_6H_5$, $R^3$=$CH_3$)

A mixture of palladium acetate (10–50 mg) and a solution of 25-ethenyl-avermectin A2 (50 mg), iodobenzene (250 mg) and triethylamine (250 mg) in acetonitrile was stirred at 60° C. for 24 hours. The reaction mixture was filtered and the filtrate was evaporated to dryness. The residue was taken up in methanol and the solution filtered and evaporated. The product, in dichloromethane, was absorbed onto a Waters silica Sep-Pak (trade mark) column, washed with dichloromethane and the crude product was eluted with ethyl acetate. Purification by reverse-phase high pressure liquid chromatography on a 1 inch Dupont Zorbax (trade mark) ODS C18 column eluting with mixtures of methanol and water gave the product as a white solid (24 mg).

A range of similar compounds were prepared by the same method and on the same scale using the appropriate aryl iodide. Data are provided in Table 1.

TABLE 1

| Example | C-25 Substituent | Class | Yield | $^1$H NMR signals for C-25 side-chain | FAB MS Ion observed/theor. | EI MS Fragmentation pattern |
|---|---|---|---|---|---|---|
| 9 | 2-Phenylethenyl | A2 | 24 mg | 7.4 (m,5H), 6.7 (d,1H), 6.25 (dd,1H) | 973/973 | 369, 351, 337, 303, 215, 145, 129, 113, 95, 87 |
| 10 | 2-Phenylethenyl | B1 | 22 mg | 7.4 (m,5H), 6.7 (d,1H), 6.3 (dd,1H) | 941/941 | 351, 267, 218, 197, 169, 145, 127, 113, 95, 87 |
| 11 | 2-(4-Fluorophenyl)-ethenyl | A2 | 18 mg | 7.4 (m,2H), 7.04 (m,2H), 6.66 (d,1H), 6.16 (dd,1H) | 991/991 | 662, 369, 303, 145 127, 113, 95, 87 |
| 12 | 2-(4-Methylthiophenyl)-ethenyl | A2 | 17 mg | 7.35 (m, 2H), 7.22 (m, 2H) 6.64 (d,1H) 6.2 (dd,1H), 2.52 (s,3H) | 1019/1019 | 415, 190, 178, 145, 113 87 |
| 13 | 2-(4-Methoxyphenyl)-ethenyl | A2 | 30 mg | 7.38 (d,2H), 6.88 (d,2H), 6.63 (d,1H), 6.1 (dd,1H), 3.75 (s,3H) | 1003/1003 | 381, 315, 175, 161, 145, 113, 95, 87 |
| 14 | 2-(4-hydroxymethylphenyl)-ethenyl | A2 | 14 mg | 7.45 (d,2H), 7.36 (d,2H), 6.7 (d,1H), 6.25 (dd,1H), 4.7 (s,2H) | 1003/1003 | 362, 312, 259, 209, 145, 87 |
| 15 | 2-(4-aminosulphonylphenyl)-ethenyl | A2 | 22 mg | 7.8 (d,2H), 7.58 (d,2H), 6.77 (d,1H), 6.42 (dd,1H) | 1052/1052 | 351, 290, 242, 225, 145, 113, 87 |
| 16 | 2-(4-acetylphenyl)-ethenyl | A2 | 25 mg | 7.95 (d, 2H), 7.55 (d, 2H), 6.75 (d, 1H), 6.41 (dd, 1H), 2.62 (s, 3H) | 1015/1015 | 393, 309, 187, 171, 145, 127, 113, 95, 87 |
| 17 | 2-(4-nitrophenyl)-ethenyl | A2 | 25 mg | 8.22 (d,2H), 7.58 (d,2H) 6.8 (d,1H), 6.5 (dd,1H), | 1018/1018 | 396, 312, 275, 257, 145, 127, 113, 95, 87 |
| 18 | 2-(4-trifluoro- | A2 | 17 mg | 7.5 (d,2H), 7.2 | 1057/1057 | 435, 369, 351, 323, |

TABLE 1-continued

| Example | C-25 Substituent | Class | Yield | $^1$H NMR signals for C-25 side-chain | FAB MS Ion observed/theor. | EI MS Fragmentation pattern |
|---------|------------------|-------|-------|----------------------------------------|----------------------------|------------------------------|
|         | methoxyphenyl)-ethenyl |  |  | (d,2H), 6.7 (d,1H), 6.25 (dd,1H), |  | 257, 145, 127, 113, 95, 87 |
| 19 | 2-(4-trifluoro-methoxyphenyl)-ethenyl | B1 | 19 mg | 7.48 (d,2H), 7.2 (d,2H), 6.7 (d,1H), 6.28 (dd,1H), | 1025/1025 | 696, 281, 215, 145, 113, 87 |
| 20 | 2-(4-methoxy-carbonylphenyl)-ethenyl | A2 | 19 mg | 8.01 (d, 2H), 7.44 (d, 2H), 6.75 (d, 1H), 6.4 (dd, 1H), 3.92 (s, 3H) | 1031/1031 | 702, 409, 377, 343, 325, 203, 171, 145, 127, 113, 95, 87 |
| 21 | 2-(4-formyl-phenyl)-ethenyl[(1)] | A2 | 9 mg | 10.02 (s,1H), 7.88 (d,2H), 7.5 (d,2H), 6.78 (d,1H), 6.45 (dd,1H) | 1001/1001 | 672, 379, 225, 173, 145, 127, 113, 95, 87 |
| 22 | 2-(methoxycarbonyl)-ethenyl[(2)] | B1 | 5 mg | 7.09 (dd,14), 6.22 (d,14), 3.8 (s,3H) | 923/923 | 275, 267, 249, 239, 221, 197, 179, 145, 127, 113, 111, 95, 87 |

[(1)]By-product formed during the synthesis of Compound 14.
[(2)]Prepared at room temperature without triethylamine using methoxycarbonylmercuric acetate in place of the aryl iodide.

EXAMPLES 23-28

25-(1-Methyl-3-phenyl-but-3-enyl)-avermectin A2 and 25-(1-methyl-4-phenyl-but-3-enyl)-avermectin A2 (formula I, $R^1$=OH, double bond absent, $R^3$=CH$_3$ and $R^2$=—CH(CH$_3$)CH$_2$C(C$_6$H$_5$)=CH$_2$ and —CH(CH$_3$)CH$_2$CH=CHC$_6$H$_5$ respectively)

A mixture of palladium acetate (10–50 mg) and a solution of 25-(1-methylbut-3-enyl)-avermectin A2 (50 mg), iodobenzene (250 mg) and triethylamine (250 mg) in acetonitrile was stirred at 60° C. for 6 hours. The reaction mixture was then filtered and the filtrate was evaporated to dryness and taken up in methanol. The solution was filtered and evaporated and the residue taken up in dichloromethane. This was applied to a Waters silica Sep-Pak (trade mark) column, washed through with dichloromethane and the crude product was eluted with ethyl acetate. The product was obtained as a mixture of the 3-phenyl and 4-phenyl isomers (approximate ratio 1:3). The components were separated by reverse-phase high pressure liquid chromatography on a Dupont Zorbax (trade mark) ODS C18 column eluting with mixtures of methanol and water. Evaporation of the appropriate product-containing fractions gave the title 3-phenyl isomer (7 mg) and 4-phenyl isomer (18 mg) as white solids.

A range of similar compounds were prepared by the same method and on the same scale using the appropriate aryl iodide. Data are provided in Table 2.

TABLE 2

| Example | C-25 Substituent | Class | Yield | $^1$H NMR signals for C-25 side-chain | FAB MS Ion observed/theor. | EI MS Fragmentation pattern |
|---------|------------------|-------|-------|----------------------------------------|----------------------------|------------------------------|
| 23 | 1-Methyl-3-phenyl-but-3-enyl | A2 | 7 mg | 7.2–7.45 (5H,m), 5.4 (1H,s), 5.08 (1H,s), 0.72 (3H,d) | 1015/1015 | 411, 393, 205, 145, 113, 87 |
| 24 | 1-Methyl-4-phenyl-but-3-enyl | A2 | 18 mg | 7.2–7.45 (5H,m), 6.5 (1H,d), 6.3 (1H,dd), 0.9 (3H,d) | 1015/1015 | 411, 393, 145, 117, 87 |
| 25 | 1-Methyl-3-(4-fluorophenyl)-but-3-enyl | A2 | 6 mg | — | 1033/1033 | 429, 411, 345, 215, 145, 87 |
| 26 | 1-Methyl-4-(4-fluorophenyl)-but-3-enyl | A2 | 14 mg | 7.3 (2H,m), 7.0 (2H,m), 6.45 (1H,d), 6.1 (1H,dd), 0.95 (3H,d), | 1033/1033 | 704, 411, 354, 345, 327, 317, 275, 233, 215, 211, 145, 87 |
| 27 | 1-Methyl-4-(4-methylthio-phenyl)-but-3-enyl | A2 | 15 mg | 7.28 (2H,d), 7.2 (2H,d), 6.43 (1H,d), 6.27 (1H,m), 2.5 (3H,s), 0.95 (3H,s) | 1061/1061 | 457, 439, 373, 355, 345, 327, 278, 243, 163, 145, 115, 113, 95, 87 |
| 28 | 1-Methyl-4-(4-amino-sulphonylphenyl)-but-3-enyl | A2 | 20 mg | 7.89 (2H,d), 7.57 (2H,d), 6.65 (1H,m), 6.45 (1H,d), 1.1 (3H,d), | 1094/1094 | 411, 240, 145, 113, 87 |

EXAMPLE 29

25-[2-(3-Pyridyl)-ethenyl]-avermectin A2 (formula I, $R^1$=OH, double bond absent, $R^2$=—CH=CH(C$_5$H$_4$N), $R^3$=CH$_3$)

A mixture of palladium acetate (10–50 mg), tri-o-tolylphosphine (10–50 mg) and a solution of 25-ethenyl-avermectin A2 (50 mg), 3-bromopyridine (250 mg) and triethylamine (250 mg) in acetonitrile was stirred at reflux under nitrogen for 24 hours. The reaction mixture was cooled and filtered and the filtrate was evaporated to dryness. The residue was then partitioned between dichloromethane and aqueous sodium bicarbonate. The organic phase was dried and evaporated and the residue was purified by reverse phase high pressure liquid chromatography on a Dupont Zorbax (trade mark) C18 ODS column eluting with a mixture of methanol/water/triethylamine. Evaporation of the appropriate fractions yielded the product (12.5 mg) as a white solid.

FAB mass spectrometry: Observed (M+Na+) 974 (theoretical 974).

EI mass spectrometry: 644, 612, 312, 370, 352, 240, 215, 145, 113, 95, 87.

$^1$H NMR as expected for an A2 avermectin subclass, with characteristic peaks for the C-25 side-chains at 8.68, 8.5, 7.76 and 7.28 (4m, 4H), 6.7 (d, 1H), 6.34 (dd, 1H).

PREPARATION 1

25-(1-Methylbut-3-enyl)avermectins A2 and B1

A frozen inoculum (2 ml) of a culture of *Streptomyces avermitilis* mutant organism ATCC 53568 was inoculated into 100 mls of a medium containing starch (2 g), Pharmamedia (Trademark) 1.5 g, ardamine pH (0.5 g) and calcium carbonate, and incubated in two 300 ml Erlenmeyer flasks at 28° C. on a rotary shaker with a 2.5 cm throw at 170 r.p.m. for 2 days. The resultant vegetative growth was used to inoculate at a rate of 5% two Fernbach flasks containing 1 liter each of the seed medium for preparation of the second seed culture. These flasks were incubated under the same conditions, and after two days the total contents transferred to a 100 liter vessel containing 70 liters of the same medium and incubated at 28° C., for 2 days, with agitation at 350 r.p.m. and aeration at 70 liters/min. This third stage seed culture was then inoculated into a 2000 liter fermenter containing 1200 liters of a medium consisting of starch (100 kg), dipotassium hydrogen phosphate (1.2 kg), ferrous sulphate (120 g), calcium carbonate (8.4 kg) glutamic acid (0.72 kg), and manganous sulphate (120 g) at pH 7.0. 2-Methylpent-4-enoic acid (480 g) was added after 96 hours and again after 168 hours (240 g) and 216 hours (126 g). After 288 hours the mycelium was removed by filtration and extracted with acetone (2×410 liters). The acetone extract was concentrated to approximately 200 liters and extracted with ethyl acetate (3×205 liters). The combined ethyl acetate layers were concentrated to 10 liters and 10 liters methanol and 0.5 liters water were added. This solution was extracted with 20 liters hexane and the hexane layer separated and back-washed with 10 liters methanol and 0.5 liters water. The combined aqueous methanol layers were evaporated to dryness to give a dark brown oil (362 g). This oil was dissolved in dichloromethane (1.2 liters) and stirred for 1 hour with silica gel (300 g) and charcoal (150 g). The suspension was filtered and the filtrate evaporated to give a brown oil (275 g). A solution of this oil in isopropyl ether (350 ml) was dripped into stirred hexane (5 liters) at 10° C. After allowing the suspension to stand at 10° C. overnight the precipitated light brown powder (173.4 g) was recovered by filtration. This crude product was then chromatographed to isolate the individual avermectin subclasses. 15 g Batches of the mixture were dissolved in 25-50 ml ethyl acetate and a little hexane. This was then added to a Prep 500 normal phase high pressure liquid chromatography column eluting with a 1:1 mixture of ethyl acetate and hexane at a flow rate of 150 ml/min to give fractions highly enriched in the different subclasses.

Batches (1 g) of material, obtained as above, enriched in the A2 component were further purified on a Dynamax (trade mark) reverse phase high pressure liquid chromatography column by elution with a 78:22 mixture of methanol and water at a flow rate of 45 ml/min. Appropriate fractions were combined and evaporated to yield approximately 350 mg of 25-(1-methylbut-3-enyl) avermectin A2 in >95% purity.

FAB mass spectrometry: (M+ +Na) observed at m/z 939 (theoretical 939).

EI mass spectrometry: 610, 335, 317, 233, 179, 145, 139, 113, 95, 87.

$^1$H NMR (CDCl$_3$) 5.85 (1H, m, C$\underline{H}$=CH$_2$), 5.1 (2H, m, CH=C$\underline{H}_2$), 0.92 (3H, d, —CHC$\underline{H}_3$—).

The B1 enriched material (21 mg) was chromatographed on a C-18 Ultrasphere (trade mark, Beckman) column (10 mm×25 cm) eluting with a gradient of methanol and water from (75:25) to (90:10) over 90 minutes at 4 ml/min. Appropriate fractions were combined and evaporated to give 25-(1-methylbut-3-enyl)avermectin B1 (7 mg).

FAB mass spectrometry: (M+ +Na) observed at m/z 907 (theoretical 907).

EI mass spectrometry: 596, 578, 317, 261, 257, 233, 205, 145, 127, 113, 95 and 87.

$^1$H NMR (CDCl$_3$) 5.85 (1H, m, C$\underline{H}$=CH$_2$), 5.1 (2H, m, CH=C$\underline{H}_2$), 0.92 (3H, d, —CHC$\underline{H}_3$).

PREPARATION 2

25-(1-Methylthioethyl)avermectin A2 and B1

The procedure of Preparation 1 was followed but adding methylthiolactic acid to the fermentation in place of 2-methylpent-4-enoic acid. The crude product (100 g), following precipitation from hexane, was chromatographed on silica gel (1 kg). The column was washed with diethyl ether/hexane (1:1) and the product then eluted with diethyl ether (7 liters) followed by ethyl acetate/diethylether (1:2, 3.5 liters) and ethyl acetate (3.75 liters). Fractions (250 ml) were collected. Fractions 19 to 31 were combined and evaporated to give a solid which consisted of a mixture of 25-(1-methylthioethyl)avermectin A2 and 25-(1-methylthioethyl)avermectin B1, (13 g). Fractions 32 to 39 were combined and evaporated to give a solid which contained 25-(1-methylthioethyl)avermectin B1, (3.49).

The later product (1.5 g) was further purified by high pressure liquid chromatography, on a C-18 Dynamax (trade mark Rainin) column (41.4 mm×25 cm) eluting with a gradient of methanol and water from (75:25) to (80:20) over 104 minutes at a flow rate of 45 ml/min. Appropriate fractions were combined and evaporated to yield 360 mg of 25-(1-methylthioethyl)avermectin B1.

FAB mass spectrometry: (M+ +Na) observed at m/z 913 (theoretical 913).

EI mass spectrometry: 584, 323, 261, 257, 233, 205, 145, 127, 113, 95 and 87.

$^1$H NMR (CDCl$_3$) 2.2 (3H, s, C$\underline{H}_3$—S) 1.13 (3H, d, CH$_3$SCHC$\underline{H}_3$).

Fractions 19 to 31 from the silica gel chromatography were further purified by chromatography on a C-18 Micro-Bondapack (trade mark) column (50 mm×50 cm) in a water Prep 500 high pressure liquid chromatograph eluting with a mixture of methanol and water (77:23) at 50 ml/min. followed by chromatography of the A2 enriched fractions on a C-18 Dynamax (trade mark Rainin) column (41.4 mm×25 cm) eluting with a gradient of methanol and water from 28:72 to 20:80 over 138 minutes at 45 ml/min. Appropriate fractions were combined to give 25-(1-methylthioethyl)avermectin A2 (320 mg).

FAB mass spectrometry: (M+ +Na) observed at m/z 945 (theoretical 945).

EI mass spectrometry: 341, 323, 275, 263, 257, 239, 211, 187, 179, 145, 113, 111, 95 and 87.

$^1$H NMR (CDCl$_3$) 2.18 (3H, s, C$\underline{H}_3$—S), 1.13 (3H, d, CH$_3$SCHC$\underline{H}_3$).

TEST PROCEDURE

Anthelmintic Activity

Anthelmintic activity was evaluated against *Caenorhabditis elegans* using the in vitro screening test described by K. G. Simpkin and G. L. Coles in Parasitology, 1979, 79, 19, with a well concentration of 1 microgram per ml.

Insecticidal Activity

Activity against the larval stage of the blowfly *Lucilia cuprina* (Q strain) is demonstrated using a standard procedure in which first instar larvae are kept in contact with filter paper treated with test compound. The test compound is first applied to the paper as an acetone solution to give a concentration of the test compound of 1 milligram per square meter. The treated filter papers are then placed into tubes containing 1 ml of newborn calf serum and the first instars are added. The tubes are examined after 24 hours and the % of larvae killed recorded.

The compounds of the invention are active in the above tests, for most compounds, 100% of the worms or larvae were killed at the concentration of test compound stated.

We claim:

1. A compound having the formula:

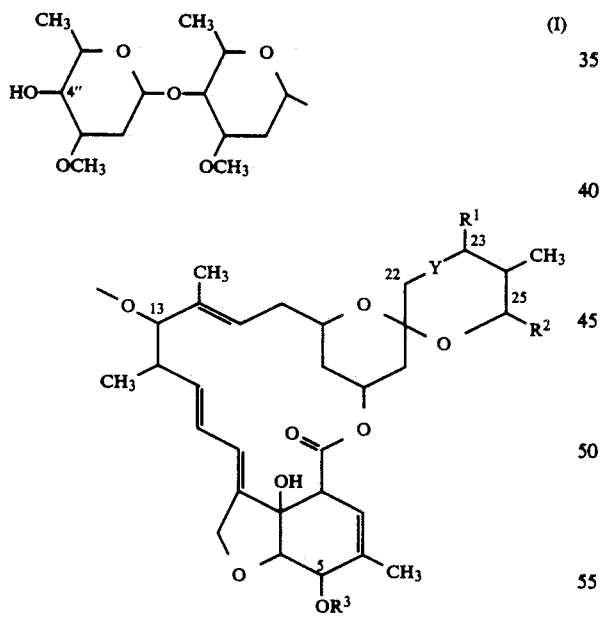

wherein Y is a single bond or a double bond; R$^1$ is OH; provided that when Y is a single bond R$^1$ is present and when Y is a double bond R$^1$ is absent; R$^2$ is =CH$_2$, —CH=CH$_2$ or —(X)—C(R$^5$)=CHR$^6$; R$^3$ is H or CH$_3$; one of R$^5$ and R$^6$ is H and the other is C$_2$-C$_6$ alkoxycarbonyl, pyridyl, phenyl or substituted phenyl, wherein the substituent is fluorine, chlorine, C$_1$-C$_4$ alkyl, C$_1$-C$_4$ alkoxy, C$_1$-C$_4$ alkylthio, hydroxy(C$_1$-C$_4$)alkyl, formyl, ammosulphonyl, C$_2$-C$_6$ alkanoyl, C$_2$-C$_6$ alkoxycarbonyl, nitro, trifluoromethyl or trifluoromethoxy; and X is a direct bond or an alkylene group having from 2 to 6 carbon atoms which may be straight or branched chain.

2. A compound according to claim 1 wherein R$^2$ is =CH$_2$.

3. The compound according to claim 2 wherein Y is a single bond; R$^1$ is present and is OH; and R$^3$ is methyl.

4. A compound according to claim 1 wherein R$^2$ is

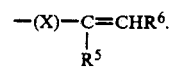

5. A compound according to claim 1 wherein R$^2$ is —CH=CH$_2$.

6. The compound according to claim 5 wherein Y is a double bond and R$^1$ is absent; and R$^3$ is hydrogen.

7. The compound according to claim 5 wherein R$^3$ is methyl; Y is a single bond; and R$^1$ is present and is OH.

8. A compound according to claim 4 wherein X is a direct bond; R$^5$ is hydrogen; and R$^6$ is substituted phenyl.

9. A compound according to claim 8 wherein R$^6$ is 4-trifluoromethoxyphenyl.

10. The compound according to claim 9 wherein R$^3$ is hydrogen; and Y is a double bond and R$^1$ is absent.

11. A compound according to claim 8 wherein R$^6$ is 4-fluorophenyl.

12. A compound according to claim 4 wherein X is a direct bond; R$^5$ is hydrogen; and R$^6$ is pyridyl.

13. The compound according to claim 12 wherein R$^6$ is 3-pyridyl; R$^3$ is methyl; Y is a single bond; and R$^1$ is present and is OH.

14. A compound having the formula

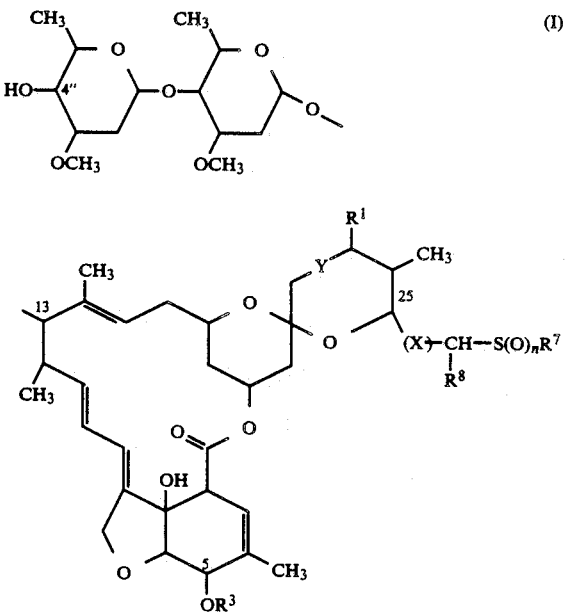

wherein
Y is a single bond or a double bond; R$^1$ is OH; provided that when Y is a single bond R$^1$ is present, and when Y is a double bond R$^1$ is absent;
X is a direct bond or an alkylene group having from 2 to 6 carbon atoms which may be straight or branched-chain; R$^7$ is C$_1$-C$_4$ alkyl; R$^8$ is H or C$_1$-C$_4$ alkyl; and n is 1 or 2.

15. A compound according to claim 14 wherein each of $R^7$ and $R^8$ is $C_1$-$C_4$ alkyl and X is a direct bond.

16. The compound according to claim 15 wherein each of $R^7$ and $R^8$ is methyl; n is 1; $R^3$ is hydrogen; Y is a double bond and $R^1$ is absent.

17. A compound according to claim 14 wherein $R^7$ is methyl; $R^8$ is hydrogen; and n is 1.

18. A composition for the treatment of parasitic infections in humans and animals and for treating agricultural pests and insects, said composition comprising an inert diluent or carrier and an antiparasitic amount of a compound of the formula

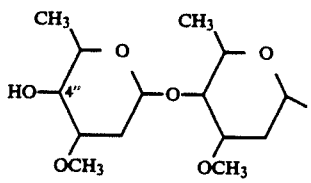

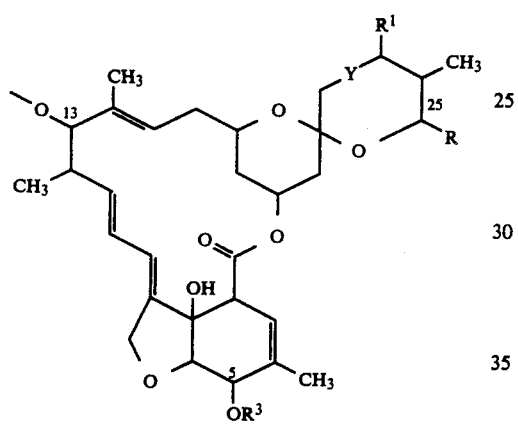

wherein
Y is a single bond or a double bond; $R^1$ is OH; provided that when Y is a single bond $R^1$ is present; and when Y is a double bond $R^1$ is absent;
$R^3$ is H or $CH_3$;
R is $=CH_2$, $-CH=CH_2$, $-(X)-C(R^5)=CHR^6$ or $-(X)-CH(R^8)-S(O)_nR^7$; wherein X is a direct bond or an alkylene group having from 2 to 6 carbon atoms which may be straight or branched-chain; one of $R^5$ and $R^6$ is H and the other is $C_2$-$C_6$ alkoxycarbonyl, pyridyl, phenyl or substituted phenyl wherein the substituent is fluorine, chlorine, $C_1$-$C_4$ alkyl, $C_1$-$C_4$ alkoxy, $C_1$-$C_4$ alkylthio, hydroxy($C_1$-$C_4$)alkyl, formyl, aminosulphonyl, $C_2$-$C_6$ alkanoyl, $C_2$-$C_6$ alkoxycarbonyl, nitro, trifluoromethyl or trifluoromethoxy;
$R^7$ is $C_1$-$C_4$ alkyl;
$R^8$ is H or $C_1$-$C_4$ alkyl and n is 1 or 2.

19. A composition according to claim 18 in the form of a liquid drench, an oral or parenteral formulation, an animal feedstuff or a premix or supplement for addition to animal feed.

20. A method of treating parasite infections, or pest or insect infestations, which comprises contacting the organism responsible for said infection or infestation or the location of said organism with a parasite infection treating or pest or insect infestation treating amount of a compound of the formula

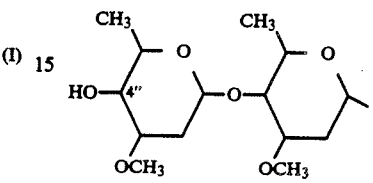

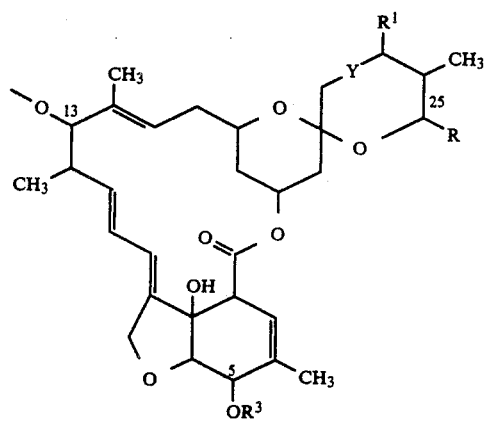

wherein
Y is a single bond or a double bond; $R^1$ is OH; provided that when Y is a single bond $R^1$ is present; and when Y is a double bond $R^1$ is absent;
$R^3$ is H or $CH_3$;
R is $=CH_2$, $-CH=CH_2$, $-(X)-C(R^5)=CHR^6$ or $-(X)-CH(R^8)-S(O)_nR^7$; wherein X is a direct bond or an alkylene group having from 2 to 6 carbon atoms which may be straight or branched-chain; one of $R^5$ and $R^6$ is H and the other is $C_2$-$C_6$ alkoxycarbonyl, pyridyl, phenyl or substituted phenyl, wherein the substituent is fluorine, chlorine, $C_1$-$C_4$ alkyl, $C_1$-$C_4$ alkoxy, $C_1$-$C_4$ alkylthio, hydroxy($C_1$-$C_4$)alkyl, formyl, aminosulphonyl, $C_2$-$C_6$ alkanoyl, $C_2$-$C_6$ alkoxycarbonyl, nitro, trifluoromethyl or trifluoromethoxy;
$R^7$ is $C_1$-$C_4$ alkyl;
$R^8$ is H or $C_1$-$C_4$ alkyl and n is 1 or 2.

* * * * *

UNITED STATES PATENT AND TRADEMARK OFFICE
CERTIFICATE OF CORRECTION

PATENT NO. : 4,992,424

DATED : February 12, 1991

INVENTOR(S) : Bernard J. Banks et al.

It is certified that error appears in the above-identified patent and that said Letters Patent is hereby corrected as shown below:

At Column 13, line 3, delete "312,".

Signed and Sealed this

Twenty-ninth Day of September, 1992

Attest:

DOUGLAS B. COMER

*Attesting Officer*    Acting Commissioner of Patents and Trademarks